United States Patent
Cho et al.

(10) Patent No.: US 7,241,906 B2
(45) Date of Patent: Jul. 10, 2007

(54) BYCYCLIC TETRAHYDROFURAN DERIVATIVES AND PROCESS FOR THE PREPARATION THEREOF

(75) Inventors: Yong Seo Cho, Seoul (KR); Ae Nim Pae, Seoul (KR); Joo Hwan Cha, Seoul (KR); Hun Yeong Koh, Seoul (KR); Chul Shin, Incheon (KR)

(73) Assignee: Korea Institute of Science and Technology, Seoul (KR)

( * ) Notice: Subject to any disclaimer, the term of this patent is extended or adjusted under 35 U.S.C. 154(b) by 48 days.

(21) Appl. No.: 11/300,966

(22) Filed: Dec. 15, 2005

(65) Prior Publication Data

US 2007/0010576 A1 Jan. 11, 2007

(30) Foreign Application Priority Data

Jul. 8, 2005 (KR) .................... 10-2005-0061697

(51) Int. Cl.
*C07D 493/02* (2006.01)

(52) U.S. Cl. ...................... 549/464; 549/396
(58) Field of Classification Search ............... 549/396, 549/464
See application file for complete search history.

(56) References Cited

U.S. PATENT DOCUMENTS

2007/0010679 A1* 1/2007 Cho et al. .................... 549/283

OTHER PUBLICATIONS

Masayuki, Sataki, Azaspiracid, a New Marine Toxin Having Unique Spiro Ring Assemblies, Isolated from Irish Mussels, *Mytilus edulis*, J. Am. Chem. Soc., 1998, 120, 9967-9968.

Josep Aiguade, Synthesis of a 2,9-Dioxabicyclo[3..3.1]nonane via Double Intramolecular Hetero-Michael Addition: Entry to the F-G Ring System of the Azaspiracids, Org. Lett., 2001, 3, 979-982.

K.C. Nicolaou, Synthesis of the FGHI Ring System of Azaspiracid, Angew. Chem., Int. Ed. 2001,40, 1262-1265.

Stephen Hanessian, Total Synthesis and Structural Confirmation of Malayamycin A: A Novel Bicyclic C-Nucleoside from *Streptomyces malaysiensis*, Org. Lett., 2003, 23, 4277-4280.

* cited by examiner

*Primary Examiner*—Amelia A. Owens
(74) *Attorney, Agent, or Firm*—Frommer Lawrence & Haug LLP; Ronald R. Santucci

(57) ABSTRACT

The present invention relates to bicyclic tetrahydrofuran derivatives of Formula (1) and a preparation method thereof, and particularly it relates to a process of preparing compounds of Formula (1) by performing an intramolecular cyclization of tetrahydrofuran-allenol derivatives in the presence of alcohol compound, transitional metal catalyst and carbon monoxide:

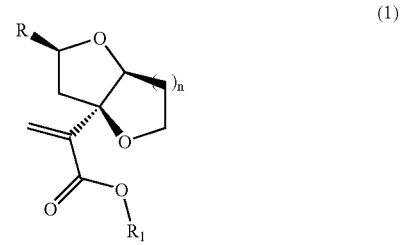

(1)

wherein n is 1 or 2; R is phenyl optionally substituted with $C_1$-$C_6$ alkyl, $C_1$-$C_6$ alkoxy, hydroxyl or $C_1$-$C_6$ hydroxyalkyl group; and $R_1$ is $C_1$-$C_6$ alkyl group.

10 Claims, No Drawings

BYCYCLIC TETRAHYDROFURAN DERIVATIVES AND PROCESS FOR THE PREPARATION THEREOF

This application claims priority benefits from South Korean Patent Application No. 10-2005-0061697 filed Jul. 8, 2005.

TECHNICAL FIELD

The present invention relates to bicyclic tetrahydrofuran derivatives of Formula (1) and a preparation method thereof, and particularly it relates to a process of preparing compounds of Formula (1) by performing an intramolecular cyclization of tetrahydrofuran-allenol derivatives in the presence of alcohol compound, transitional metal catalyst and carbon monoxide:

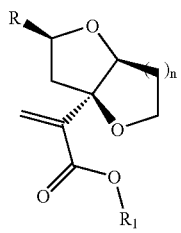

(1)

wherein n is 1 or 2; R is phenyl optionally substituted with $C_1$-$C_6$ alkyl, $C_1$-$C_6$ alkoxy, hydroxyl or $C_1$-$C_6$ hydroxyalkyl group; and $R_1$ is $C_1$-$C_6$ alkyl group.

RELATED PRIOR ART

Tetrahydrofuran derivatives are known to exist in various natural substances, and are investigated as active ingredients in natural substances or synthetic drugs. Especially, stereoselective tetrahydrofuran derivatives having cis geometry at C-2,5 positions are known to have superior bioactivity. For example, bicyclic tetrahydrofuran or bicyclic perhydrofuropyran compounds serve a structural basis of various natural substances (*J. Am. Chem. Soc.*, 1998, 120, 9967-9968; *Org. Lett.*, 2001, 3, 979-982; *Angelic. Chem., Int. Ed.* 2001, 40, 1262-1265).

However, the conventional process for preparing bicyclic tetrahydrofuropyran (*Org. Lett.*, 2003, 5, 4277-4280) utilizes a complicated multi-step synthesis, thus placing a limit in its industrial application.

Therefore, there is still a demand to develop bicyclic tetrahydrofuran derivatives highly useful as key materials in the pharmaceutical or fine chemical industry, and a more efficient process for preparing the compounds.

SUMMARY OF INVENTION

In one aspect of the present invention, there are provided bicyclic tetrahydrofuran derivatives with a novel structure.

In another aspect of the present invention, there is provided a process for preparing the bicyclic tetrahydrofuran derivatives by performing intramolecular cyclization of tetrahydrofuran comprising allenol in the presence of alcohol compound, transitional metal catalyst and carbon monoxide.

DETAILED DESCRIPTION

In one aspect, the present invention relates to bicyclic tetrahydrofuran derivatives of Formula (1):

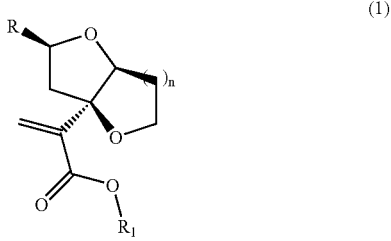

(1)

wherein n is 1 or 2; R is phenyl optionally substituted with $C_1$-$C_6$ alkyl, $C_1$-$C_6$ alkoxy, hydroxyl or $C_1$-$C_6$ hydroxyalkyl group; and $R_1$ is $C_1$-$C_6$ alkyl group.

The bicyclic tetrahydrofuran derivatives of the present invention are novel compounds with a novel structure and are highly useful value as active materials in the pharmaceutical or fine chemical industry.

The bicyclic tetrahydrofuran derivatives of Formula (1) includes without limitation those (i) wherein n is 1, R is phenyl optionally substituted with $C_1$-$C_6$ alkyl or $C_1$-$C_6$ alkoxy group, and $R_1$ is $C_1$-$C_6$ alkyl group, or (ii) wherein n is 2, R is phenyl optionally substituted with $C_1$-$C_6$ alkyl or $C_1$-$C_6$ alkoxy group, and $R_1$ is $C_1$-$C_6$ alkyl group.

In another aspect, the present invention relates to a process of preparing bicyclic tetrahydrofuran derivatives of Formula (1), the process comprising an intramolecular cyclization of tetrahydrofuran-allenol derivatives of Formula (2) in the presence of alcohol compound, transitional metal catalyst and carbon monoxide:

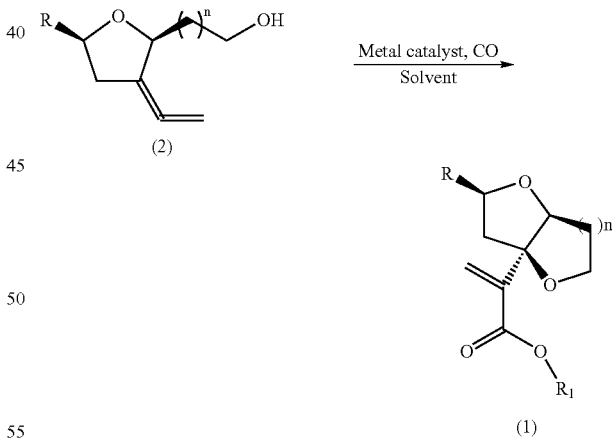

wherein n, R and $R_1$ are same as defined above.

The alcohol compound is used for introducing $R_1$, and selected from $C_1$-$C_6$ alkyl alcohol. The amount of the used alcohol compound may be from 1 equivalent to a solvent amount, preferably 1-5 equivalents with respect to the starting material, tetrahydrofuran-allenol derivatives of Formula (2).

The transitional metal catalyst is any one selected from transitional metal halides or a mixture thereof. The transitional metal catalyst is preferred to be palladium dichloride, copper dichloride or a mixture thereof. More preferably, the transitional metal catalyst is selected from the group consisting of 0.01-1 equivalent of palladium dichloride, 1-5 equivalents of copper dichloride, and a mixture thereof, with respect to tetrahydrofuran-allenol derivatives of Formula (2). Most preferably, the transitional metal catalyst is a mixture of 0.01-1 equivalent of palladium dichloride and 1-5 equivalents of copper dichloride with respect to tetrahydrofuran-allenol derivatives of Formula (2).

The alcohol compound may serve as solvent. However, if necessary, other conventional solvent may be additionally used, and the examples of the solvent include without limitation diethyl ether, tetrahydrofuran, dichloromethane, chloroform, ethyl acetate and a mixture thereof.

The intramolecular cyclization is preferred to be performed at 0-25° C. for about 3-5 hours.

EXAMPLES

The present invention is described more specifically by the following Examples. Examples herein are meant only to illustrate the present invention, but in no way to limit the claimed invention.

Example 1 methyl 2-(2-phenyl-tetrahydrofuro[3,2-b]furan-3a-yl)acrylate

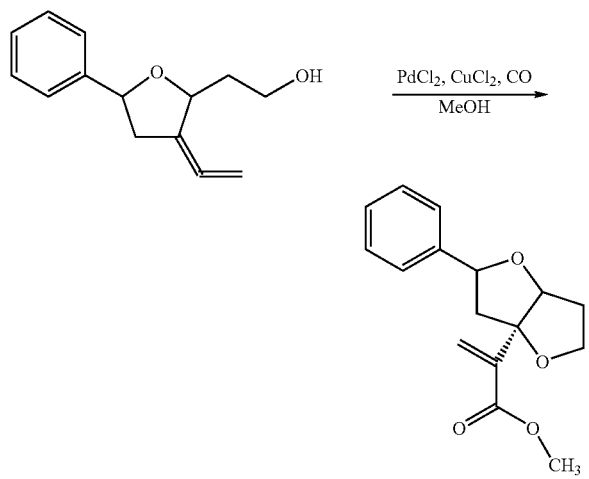

2-(5-phenyl-3-vinylidenevinylidene-tetrahydrofuran-2-yl)ethanol (39 mg, 0.18 mmol) was dissolved in 2 mL of methanol, and then was filled with CO gas (1 atm), followed by addition of PdCl$_2$ (2.4 mg, 0.014 mmol) and CuCl$_2$ (73 mg, 0.54 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (47 mg, 95%).

1H NMR (300 MHz, CDCl$_3$): δ 7.49-7.29(m, 5H), 6.39(d, 1H, J=1.5 Hz), 6.19(s, 1H), 5.35(q, 1H, J=7.2 Hz), 4.75(d, 1H, J=3.6 Hz), 4.33-4.25(m, 1H), 4.16-4.10(m, 1H), 3.86(s, 3H), 2.83(q, 1H, J=7.2 Hz), 2.64-2.16(m, 2H), 1.94-1.87(m, 1H).

Example 2 methyl 2-(2-p-tolyl-tetrahydrofuro[3,2-b]furan-3a-yl)acrylate

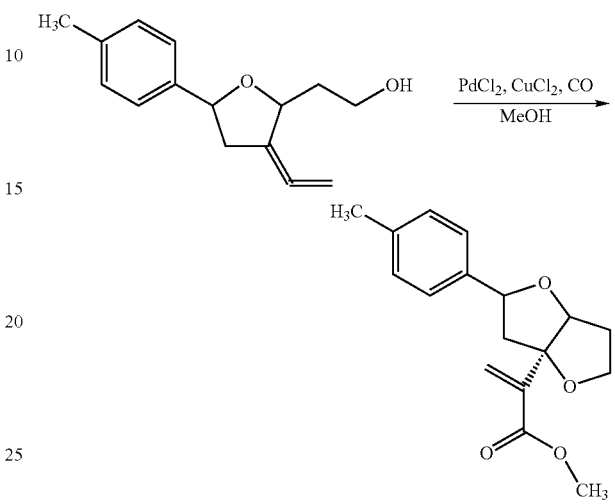

2-(5-p-tolyl-3-vinylidene-tetrahydrofuran-2-yl)ethanol (41 mg, 0.18 mmol) was dissolved in 2 mL of methanol, and then was filled with CO gas (1 atm), followed by addition of PdCl$_2$ (2.4 mg, 0.014 mmol) and CuCl$_2$ (73 mg, 0.54 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (47 mg, 91%).

1H NMR (300 MHz, CDCl$_3$): δ 7.08-7.27(m, 4H), 6.36(d, 1H), 5.67(d, 1H), 5.23(t, 1H), 4.28(m, 1H), 4.13(q, 1H), 4.02(q, 1H), 3.71(s, 3H), 2.79(m, 1H), 2.36(m, 1H), 2.34(s, 3H), 2.15(m, 1H), 1.89(m, 1H).

Example methyl 3: 2-(2-(4-methoxyphenyl)-tetrahydrofuro[3,2-b]furan-3a-yl)acrylate

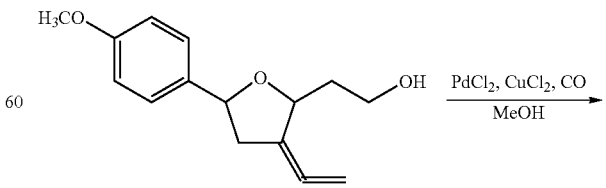

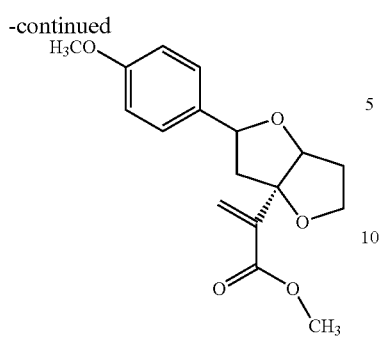

2-(5-(4-methoxyphenyl)-3-vinylidene-tetrahydrofuran-2-yl)ethanol (41 mg, 0.17 mmol) was dissolved in 2 mL of methanol, and then was filled with CO gas (1 atm), followed by addition of PdCl$_2$ (2.4 mg, 0.014 mmol) and CuCl$_2$ (73 mg, 0.54 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (45 mg, 98%).

1H NMR (300 MHz, CDCl$_3$): δ 7.21(d, 2H), 6.71(d, 1H), 6.36(d, 1H), 5.67(d, 1H), 5.17(t, 1H), 4.28(m, 1H), 4.13(q, 1H), 4.02(q, 1H), 3.79(s, 3H), 3.71(s, 3H), 2.76(m, 1H), 2.36(m, 1H), 2.15(m, 1H), 1.89(m, 1H).

Example 4 ethyl 2-(2-phenyl-tetrahydrofuro[3,2-b]furan-3a-yl)acrylate

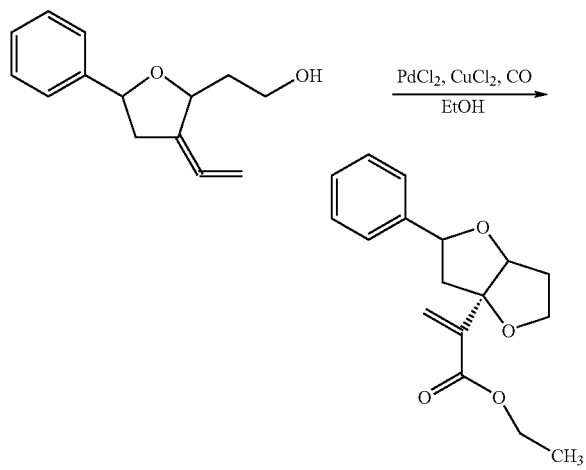

2-(5-phenyl-3-vinylidene-tetrahydrofuran-2-yl)ethanol (39 mg, 0.18 mmol) was dissolved in 2 mL of methanol, and then was filled with CO gas (1 atm), followed by addition of PdCl$_2$ (2.4 mg, 0.014 mmol) and CuCl$_2$ (73 mg, 0.54 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (47 mg, 91%)

1H NMR (300 MHz, CDCl$_3$): δ 7.49-7.29(m, 5H), 6.39(d, 1H), 6.19(s, 1H), 5.35(q, 1H), 4.75(d, 1H), 4.33-4.25(m, 1H), 4.19-4.10(m, 3H), 3.86(s, 3H), 2.83(q, 1H, J=7.2 Hz), 2.64-2.16(m, 2H), 1.94-1.87(m, 1H), 1.28(t, 3H).

Example 5 ethyl 2-(2-p-tolyl-tetrahydrofuro[3,2-b]furan-3a-yl)acrylate

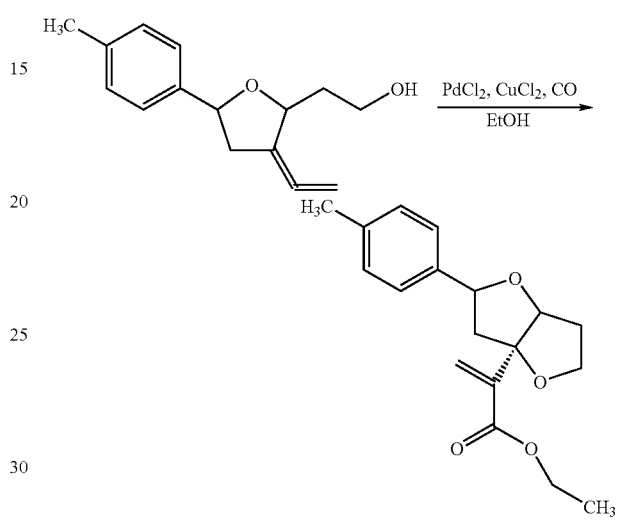

2-(5-p-tolyl-3-vinylidene-tetrahydrofuran-2-yl)ethanol (40 mg, 0.17 mmol) was dissolved in 2 mL of methanol, and then was filled with CO gas (1 atm), followed by addition of PdCl$_2$ (2.4 mg, 0.014 mmol) and CuCl$_2$ (73 mg, 0.54 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (45 mg, 87%).

1H NMR (300 MHz, CDCl$_3$): δ 7.10-7.28(m, 4H), 6.34(d, 1H), 5.66(d, 1H), 5.23(t, 1H), 4.28(m, 1H), 4.11-4.21(m, 3H), 4.02(q, 1H), 3.71(s, 3H), 2.79(m, 1H), 2.36(m, 1H), 2.34(s, 3H), 2.15(m, 1H), 1.89(m, 1H), 1.28(t, 3H).

Example 6 ethyl 2-(2-(4-methoxyphenyl)-tetrahydrofuro[3,2-b]furan-3a-yl)acrylate

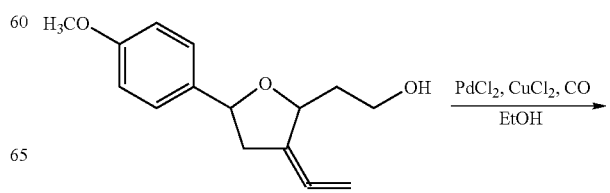

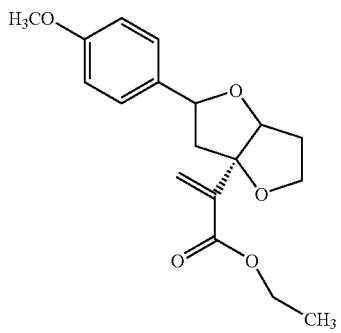

2-(5-(4-methoxyphenyl)-3-vinylidene-tetrahydrofuran-2-yl)ethanol (41 mg, 0.17 mmol) was dissolved in 2 mL of methanol, and then was filled with CO gas (1 atm), followed by addition of PdCl$_2$ (2.4 mg, 0.014 mmol) and CuCl$_2$ (73 mg, 0.54 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (46 mg, 86%).

1H NMR (300 MHz, CDCl$_3$): δ 7.20(d, 2H), 6.71(d, 1H), 6.34(d, 1H), 5.66(d, 1H), 5.15(t, 1H), 4.29(m, 1H), 4.4.11-4.21(m, 3H), 4.02(q, 1H), 3.79(s, 3H), 3.71(s, 3H), 2.76(m, 1H), 2.36(m, 1H), 2.15(m, 1H), 1.89(m, 1H), 1.28(t, 3H).

Example 7 methyl 2-(2-phenyl-hexahydrofuro[3,2-b]pyran-3a-yl)acrylate

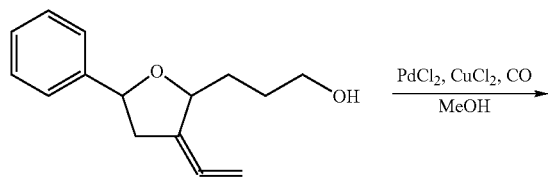

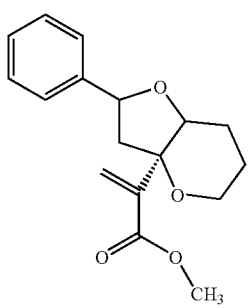

3-(5-phenyl-3-vinylidene-tetrahydrofuran-2-yl)propan-1-ol (67 mg, 0.29 mmol) was dissolved in 2 mL of methanol, and then was filled with CO gas (1 atm), followed by addition of PdCl$_2$ (5.2 mg, 0.029 mmol) and CuCl$_2$ (117 mg, 0.87 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (55 mg, 66%).

1H NMR (300 MHz, CDCl$_3$): δ 7.56(d, 2H, J=7.2 Hz), 7.41-7.27(m, 3H), 6.34(s, 1H), 5.91(s, 1H), 5.06(q, 1H, J=6.0 Hz), 4.39(t, 1H, J=2.7 Hz), 3.89-3.77(m, 4H), 3.63-3.54(m, 1H), 2.89-2.81(m, 1H), 2.33-2.14(m, 3H), 1.82-1.72(m, 1H), 1.41-1.35(m, 1H).

Example 8 methyl 2-(2-p-tolyl-hexahydrofuro[3,2-b]pyran-3a-yl)acrylate

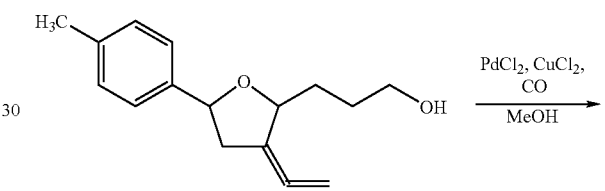

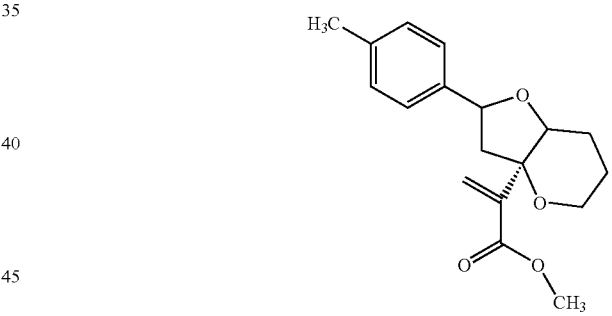

3-(5-p-tolyl-3-vinylidene-tetrahydrofuran-2-yl)propan-1-ol (65 mg, 0.26 mmol) was dissolved in 2 mL of methanol, and then was filled with CO gas (1 atm), followed by addition of PdCl$_2$ (5.2 mg, 0.029 mmol) and CuCl$_2$ (117 mg, 0.87 mmol). The solution was stirred for 4 hours at room temperature. When the reaction was completed, H$_2$O was added and the solution was stirred for 5 minutes. The mixture was diluted with ethyl acetate, washed with H$_2$O and NaCl. Organic layer was separated and dried with anhydride MgSO$_4$. Solvent was removed under reduced pressure, and the remnant was purified through silica gel tube chromatography (EtOAc:n-Hexane=1:25, v/v), thus providing products (56 mg, 70%).

1H NMR (300 MHz, CDCl$_3$): δ 7.31(d, 2H), 7.08(d, 2H), 6.30(d, 1H), 5.66(d, 1H), 5.26(t, 1H), 4.18(t, 1H), 3.70(s, 3H), 3.64-3.56(m, 2H), 2.72(m, 1H), 2.34-2.26(m, 4H), 1.98-1.65(m, 4H).

Example 9 ethyl 2-(2-phenyl-hexahydrofuro[3,2-b]pyran-3a-yl)acrylate

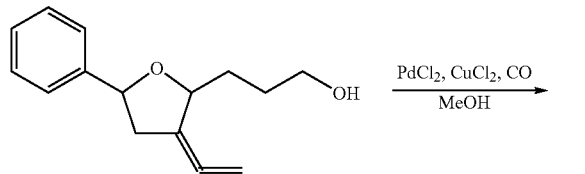

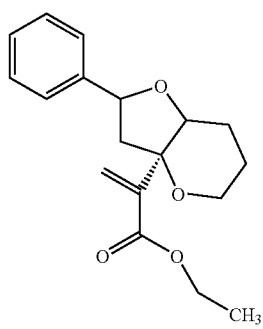

3-(5-phenyl-3-vinylidene-tetrahydrofuran-2-yl)propan-1-ol (66 mg, 0.29 mmol) was dissolved in 2 mL of methanol, and then was filled with CO gas (1 atm), followed by addition of $PdCl_2$ (5.2 mg, 0.029 mmol) and $CuCl_2$ (117 mg, 0.87 mmol). The solution was stirred for 4 hours at room temperature. When the reaction was completed, $H_2O$ was added and the solution was stirred for 5 minutes. The mixture was diluted with ethyl acetate, washed with $H_2O$ and NaCl. Organic layer was separated and dried with anhydride $MgSO_4$. Solvent was removed under reduced pressure, and the remnant was purified through silica gel tube chromatography (EtOAc:n-Hexane=1:25, v/v), thus providing products (56 mg, 65%).

1H NMR (300 MHz, $CDCl_3$): δ 7.35-7.18(m, 5H), 6.28(d, 1H), 5.65(d, 1H), 5.25(t, 1H), 4.21(q, 2H), 3.52-3.63(m, 2H), 2.76-2.71(m, 1H), 2.37-2.32(m, 1H), 1.84-1.71(m, 4H), 1.28(t, 3H).

Example 10 ethyl 2-(2-p-tolyl-hexahydrofuro[3,2-b]pyran-3a-yl)acrylate

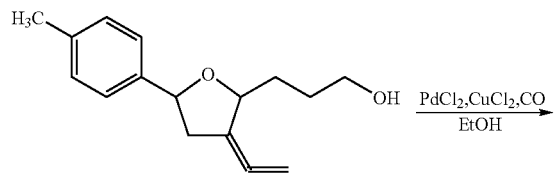

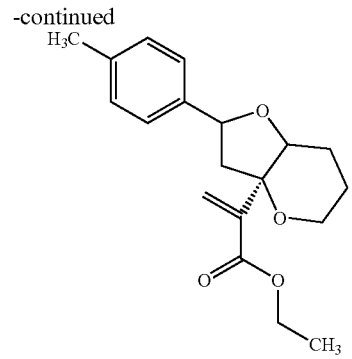

3-(5-p-tolyl-3-vinylidene-tetrahydrofuran-2-yl)propan-1-ol (65 mg, 0.26 mmol) was dissolved in 2 mL of methanol, and then was filled with CO gas (1 atm), followed by addition of $PdCl_2$ (5.2 mg, 0.029 mmol) and $CuCl_2$ (117 mg, 0.87 mmol). The solution was stirred for 4 hours at room temperature. When the reaction was completed, $H_2O$ was added and the solution was stirred for 5 minutes. The mixture was diluted with ethyl acetate, washed with $H_2O$ and NaCl. Organic layer was separated and dried with anhydride $MgSO_4$. Solvent was removed under reduced pressure, and the remnant was purified through silica gel tube chromatography (EtOAc:n-Hexane=1:25, v/v), thus providing products (58 mg, 69%).

1H NMR (300 MHz, $CDCl_3$): δ 7.31(d, 2H), 7.10(d, 2H), 6.28(d, 1H), 5.65(d, 1H), 5.29(t, 1H), 4.19(q, 2H), 3.65-3.55 (m, 2H), 2.72(m, 1H), 2.36-2.23(m, 4H), 1.96-1.64(m, 4H), 1.28(t, 3H).

As set forth above, the present invention relates to stereoselective bicyclic tetrahydrofuran derivatives with cis geometry at C-2,5, and a simple and efficient preparation method thereof by using alcohol compound, transitional metal catalyst and carbon monoxide. Especially, the bicyclic tetrahydrofuran derivatives may serve as an important intermediate compound in synthesis of natural substance.

What is claimed is:

1. Bicyclic tetrahydrofuran of Formula (1):

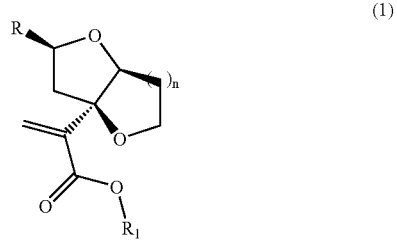

wherein n is 1 or 2; R is phenyl optionally substituted with $C_1$-$C_6$ alkyl, $C_1$-$C_6$ alkoxy, hydroxyl or $C_1$-$C_6$ hydroxyalkyl group; and $R_1$ is $C_1$-$C_6$ alkyl group.

2. The bicyclic tetrahydrofuran of claim 1, wherein n is 1; R is phenyl optionally substituted with $C_1$-$C_6$ alkyl or $C_1$-$C_6$ alkoxy group; and $R_1$ is $C_1$-$C_6$ alkyl group.

3. The bicyclic tetrahydrofuran of claim 1, wherein n is 2; R is phenyl optionally substituted with $C_1$-$C_6$ alkyl or $C_1$-$C_6$ alkoxy group; and $R_1$ is $C_1$-$C_6$ alkyl group.

4. A process of preparing bicyclic tetrahydrofuran of Formula (1), the process comprising an intramolecular cyclization of tetrahydrofuran-allenol derivatives of Formula (2) in the presence of alcohol compound, transitional metal catalyst and carbon monoxide:

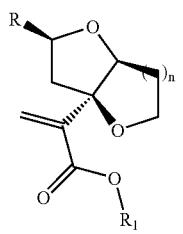

(2)

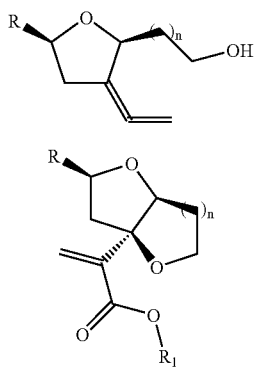

(1)

wherein n is 1 or 2; R is phenyl optionally substituted with $C_1$-$C_6$ alkyl, $C_1$-$C_6$ alkoxy, hydroxyl or $C_1$-$C_6$ hydroxyalkyl group; and $R_1$ is $C_1$-$C_6$ alkyl group.

5. The process of claim 4, wherein the alcohol compound is used in the amount of from 1 equivalent of the tetrahydrofuran-allenol of Formula (2) to a solvent amount.

6. The process of claim 4, wherein the transitional metal catalyst is transitional metal halide.

7. The process of claim 6, wherein the transitional metal catalyst is palladium dichloride, copper dichloride or a mixture thereof.

8. The process of claim 7, wherein the transitional metal catalyst is a mixture of 0.01-1 equivalent of palladium dichloride and 1-5 equivalents of copper dichloride.

9. The process of claim 4, wherein the intramolecular cyclization is performed at 0-25° C.

10. The process of claim 4, wherein any solvent selected from diethyl ether, tetrahydrofuran, dichloromethane, chloroform, ethyl acetate and a mixture thereof is additionally used.

* * * * *